United States Patent
Meredith

(10) Patent No.: US 7,115,286 B2
(45) Date of Patent: Oct. 3, 2006

(54) COMPOSITIONS AND METHODS FOR AN ORALLY ADMINISTERED INHIBITOR OF BITING INSECTS

(76) Inventor: Sarah Meredith, 24 Kendall St., Laguna Niguel, CA (US) 92677

( * ) Notice: Subject to any disclaimer, the term of this patent is extended or adjusted under 35 U.S.C. 154(b) by 10 days.

(21) Appl. No.: 10/862,261

(22) Filed: Jun. 7, 2004

(65) Prior Publication Data

US 2005/0008656 A1    Jan. 13, 2005

Related U.S. Application Data

(60) Provisional application No. 60/485,421, filed on Jul. 8, 2003.

(51) Int. Cl.
*A61K 36/00*    (2006.01)
(52) U.S. Cl. ............. 424/725; 424/195.17; 424/745; 424/747; 424/750
(58) Field of Classification Search ............. 424/725, 424/195.17, 745, 747, 750
See application file for complete search history.

(56) References Cited

U.S. PATENT DOCUMENTS 6,300,324 B1 * 10/2001 Partelow ................. 514/78

OTHER PUBLICATIONS

Internet website http://www.drgreene.org/blank.cfm (3 pages total).*
The Internet website http://www.angelfire.com/mi/peking/singa.htm (7 pages total).*
Grieve, Mrs. M.; Barley, electronic version of A Modern Herbal; 1995-2004 copyright protected; 2 pp.; Botanical.com.
Anr's Vitamins; Biotin; glossary; printed from the internet Nov. 29, 2004; 1 p.; Austin, Texas; anrvitamins.com.
Anr's Vitamins; Choline; glossary; printed from the internet Nov. 29, 2004; 1 p.; Austin, Texas; anrvitamins.com.
Anr's Vitamins; Folic Acid; glossary; printed from the internet Nov. 29, 2004; 1 pp.; Austin, Texas; anrvitamins.com.
Anr's Vitamins; Inositol; glossary; printed from the internet Nov. 29, 2004; 1 pp.; Austin, Texas; anrvitamins.com.
Grieve, Mrs. M.; Lobelia, electronic version of A Modern Herbal; 1995-2004 copyright protected; 3 pp.; Botanical.com.
Grieve, Mrs. M.; Mints, electronic version of A Modern Herbal; 1995-2004 copyright protected; 25 pp.; Botanical.com.
Fradin, Mark, S., M.D.; Mosquitoes and Mosquito Repellents: A Clinician's Guide; Jun. 1, 1998; V. 128, No. 11; pp. 931-940; Ann Intern Med.
Biotropin2000; Nutri Spray; printed from the internet Nov. 29, 2004; 2 pp.; biotropin2000.com.
Anr's Vitamins; PABA; glossary; printed from the internet Nov. 29, 2004; 1 pp.; Austin, Texas; anrvitamins.com.
Anr's Vitamins; Pantothenic Acid; glossary; printed from the internet Nov. 29, 2004; 1 pp.; Austin, Texas; anrvitamins.com.
Grieve, Mrs. M.; Parsley, electronic version of A Modern Herbal; 1995-2004 copyright protected; 6 pp.; Botanical.com.
Anr's Vitamins; Vitamin A; glossary; printed from the internet Nov. 29, 2004; 2 pp.; Austin, Texas; anrvitamins.com.
Anr's Vitamins; Vitamin B-1; glossary; printed from the internet Nov. 29, 2004; 1 pp.; Austin, Texas; anrvitamins.com.
Anr's Vitamins; Vitamin B-2; glossary; printed from the internet Nov. 29, 2004; 1 pp.; Austin, Texas; anrvitamins.com.
Anr's Vitamins; Niacin —Vitamin B-3; glossary; printed from the internet Nov. 29, 2004; 1 pp.; Austin, Texas; anrvitamins.com.
Anr's Vitamins; Vitamin B-6; glossary; printed from the internet Nov. 29, 2004; 1 pp.; Austin, Texas; anrvitamins.com.
Anr's Vitamins; Vitamin B-12; glossary; printed from the internet Nov. 29, 2004; 1 pp.; Austin, Texas; anrvitamins.com.
Anr's Vitamins; Vitamin C; glossary; printed from the internet Nov. 29, 2004; 2 pp.; Austin, Texas; anrvitamins.com.
Anr's Vitamins; Vitamin D; glossary; printed from the internet Nov. 29, 2004; 1 pp.; Austin, Texas; anrvitamins.com.

(Continued)

*Primary Examiner*—Christopher Tate
*Assistant Examiner*—S. B. McCormick-Ewoldt
(74) *Attorney, Agent, or Firm*—Faegre & Benson LLP

(57) ABSTRACT

The present disclosure concerns methods and compositions to inhibit insects from biting a subject. In preferred embodiments, the compositions may be administered orally, for example using a spray bottle to deliver to the mouth. In certain embodiments, the compositions and methods are effective to reduce swelling, itching, redness and/or inflammation of the local area of an insect bite. The compositions may include one or more herbs selected from the group consisting of rice bran, peppermint, barley grass, *lobelia; chlorella,* watercress, alfalfa and parsley and one or more vitamins selected from the group consisting of thiamin (B-1), riboflavin (B-2), niacin (B-3), pantothenic acid (B-5), pyridoxine (B-6), folic acid (B-9), cyanocobalamin (B-12), choline, inositol, d-biotin, para-aminobenzoic acid, and lecithin. Administration of effective amounts of the compositions is sufficient to inhibit insects from biting and/or treat insect affected areas of a subject.

9 Claims, No Drawings

OTHER PUBLICATIONS

Anr's Vitamins; Vitamin E; glossary; printed from the internet Nov. 29, 2004; 2 pp.; Austin, Texas; anrvitamins.com.

Grieve, Mrs. M.; Watercress, electronic version of A Modern Herbal; 1995-2004 copyright protected; 2 pp.; Botanical.com.

* cited by examiner

COMPOSITIONS AND METHODS FOR AN ORALLY ADMINISTERED INHIBITOR OF BITING INSECTS

RELATED APPLICATIONS

The present application claims the benefit under 35 U.S.C. § 119(e) of U.S. Provisional Patent Application Ser. No. 60/485,421, filed Jul. 8, 2003, the entire text of which is incorporated herein by reference.

BACKGROUND

1. Field

The following embodiments relate to inhibitors of biting insects and more particularly to compositions and methods for reducing the incidence of insect bites. Even more particularly, the disclosed compositions and methods inhibit biting insects, for example mosquitoes, from biting a subject after landing on a subject. In some embodiments, such inhibitors may also be used, for example, to reduce swelling, inflammation and/or itching after an insect bite. In various embodiments, the compositions may be administered orally to inhibit insects from biting subjects.

2. Background

Multiple species of flying and crawling insects, including mosquitoes, ticks, flies, midges, chiggers, and fleas, bite subjects, such as human subjects. Although such insects are mostly a nuisance in North America, they transmit more than 100 bacterial, protozoan, parasitic, and rickettsial diseases to humans worldwide.

Mosquitoes transmit more diseases to humans than any other biting insect. Mosquitoes are the vectors responsible for transmitting several forms of viral encephalitis, yellow fever, dengue fever, bancroftian filariasis, and epidemic polyarthritis to humans; more than 700,000,000 people are infected yearly. Malaria, which is transmitted by the bite of a mosquito infected with the single-cell protozoan *Plasmodium*, is responsible for 3,000,000 deaths annually (Fradin MS: Mosquitoes and mosquito repellents: a clinician's guide. Ann Intern Med Jun. 1, 1998 ; 128(11): 931–40).

There are over 2500 different species of mosquitoes throughout the world, of which 150 species occur in the United States. A single female mosquito can lay over 200 eggs at a time. Mosquito eggs can survive for more than five years. All mosquitoes need water to complete their life cycle. Not all species bite humans; some prefer birds, others prefer horses, and some will even bite frogs and turtles. Only females take blood; males feed only on plant nectar. Mosquitoes can fly considerable distances; some species remain close to their larval habitats while others can fly 20 miles or more. Mosquitoes do not develop in grass or shrubbery, although adults frequently rest in these areas during daylight hours. Mosquitoes are responsible for more human deaths than any other living creature.

West Nile Virus (WNV) is a flavivirus belonging taxonomically to the Japanese encephalitis serocomplex that includes the closely related St. Louis encephalitis (SLE) virus, Kunjin and Murray Valley encephalitis viruses, as well as others. WNV was first isolated in the West Nile Province of Uganda in 1937. The first recorded epidemics occurred in Israel during 1951–1954 and in 1957. Epidemics have been reported in Europe in the Rhone delta of France in 1962 and in Romania in 1996. The largest recorded epidemic occurred in South Africa in 1974.

An outbreak of arboviral encephalitis in New York City and neighboring counties in New York state in late August and September 1999, was subsequently confirmed as caused by West Nile virus, based on the identification of virus in human, avian, and mosquito samples.

Although it is not known when and how West Nile virus was introduced into North America, international travel of infected persons to New York or transport by imported infected birds may have played a role. WNV can infect a wide range of vertebrates; in humans it usually produces either asymptomatic infection or mild febrile disease, but can cause severe and fatal infection in a small percentage of patients. Within its normal geographic distribution of Africa, the Middle East, western Asia, and Europe, WNV has not been documented to cause epizootics in birds. Crows and other birds with antibodies to WNV are common, suggesting that asymptomatic or mild infection usually occurs among birds in those regions. Similarly, substantial bird virulence of SLE virus has not been reported. Therefore, an epizootic producing high mortality in crows and other bird species is unusual for either WNV or SLE virus. For both viruses, migratory birds may play an important role in the natural transmission cycles and spread. Like SLE virus, WNV is transmitted principally by *Culex* species mosquitoes, but also can be transmitted by *Aedes, Anopheles*, and other species. The predominance of urban *Culex pipiens* mosquitoes trapped during this outbreak suggests an important role for this species. By August 2002, the WNV, carried by mosquitoes, had spread to 41 states, causing a total of 24 fatalities.

Infected ticks can transmit Lyme disease, Rocky Mountain spotted fever, ehrlichiosis, babesiosis, tularemia, and tick paralysis. Flies are the vectors responsible for transmitting other diseases such as African trypanosomiasis, leishmaniasis, onchocerciasis, and loiasis to humans. Fleabites may transmit plague, and, in South America, kissing bugs transmit Chagas disease.

Despite the need for an effective oral inhibitor of biting insects, no such agent has been identified thus far. Ingested garlic, brewer's yeast, and thiamine are not effective at inhibiting insects from biting. The quest to develop the perfect topical insect repellent has been an ongoing scientific goal for years but has yet to be achieved.

The ideal insect inhibitor and/or repellent would provide protection from multiple species of biting arthropods; remain effective for at least 8 hours; cause no irritation to the skin or mucous membranes; exhibit no systemic toxicity; be resistant to abrasion and wash-off; and be greaseless and odorless, i.e., cosmetically appealing.

A distinction is made herein between insect repellents, which prevent biting insects from landing on a subject, and inhibitors of biting insects, which inhibit insects from biting a subject after landing. Although a particular composition may have efficacy as both an inhibitor and a repellant of biting insects, commercially available formulations typically act as insect repellants. Commercial insect repellents may generally be characterized as involving topical application, usually are effective for limited duration, may cause severe irritation of skin or mucous membranes, may be abraded or washed off, possess a pungent odor and greasy texture, and arguably may have toxic side effects.

To be effective, an insect repellent should be volatile enough to maintain an effective vapor concentration at the skin surface, but it must not evaporate so rapidly that it quickly loses its effectiveness. Multiple factors play a role in effectiveness, including the concentration, frequency, and uniformity of application; the user's activity level and overall attractiveness to blood-sucking arthropods; and the number and species of potentially biting insects. The effectiveness of any insect repellent is reduced by abrasion from clothing; evaporation and absorption from the skin surface; wash-off from sweat, rain, or water; a windy environment; and high ambient temperatures. Each 10° C. increase in temperature may lead to as much as a 50% reduction in protection time. (www.emedicine.com/derm/topics540.htm)

Commercial insect repellents do not cloak the user in a chemical veil of protection. Any untreated exposed skin may be readily bitten by insects. Protection from both the nuisance and the health risks associated with insect bites is presently achieved by avoiding infested habitats, wearing protective clothing, and applying an insect repellent. As discussed below, such methods are unsatisfactory for a variety of reasons.

Current Insect Repellants

DEET

Currently marketed insect repellents fall into 2 categories: manufactured (chemical) repellents and natural (plant-derived) repellents. In general, the chemical repellents have a broader spectrum of efficacy and a greater duration of action than botanical repellents.

Commercial products include OFF!™, Cutter, Repel™, Sawyer™, Ben's™ (all in multiple formulations), and Ultrathon™. Registered for use by the general public since 1957, N, N-diethyl-3-methylbenzamide (previously called N, N-diethyl-m-toluamide), or DEET, remains the standard of currently available insect repellents. DEET, a broad-spectrum repellent, is effective against many species of crawling and flying insects, including mosquitoes, biting flies, midges, chiggers, fleas, and ticks.

The Environmental Protection Agency (EPA) estimates that about 30% of the US population uses a DEET-based product every year. Worldwide use exceeds 200 million people annually. Empirical testing of more than 20,000 other compounds over the last 45 years has not led to a more effective insect repellent than DEET being brought to market.

In the United States, DEET is sold in concentrations ranging from 5–40% and 100%. DEET is available in multiple formulations, including solutions, lotions, creams, gels, aerosol and pump sprays, and impregnated towelettes. EPA regulations require that the concentration of DEET in each product be disclosed on its label.

The 3M Company manufactures a polymer-based 33% DEET cream, called Ultrathon™, which is the standard issue repellent given to the US military. When tested under multiple environmental and climatic field conditions, Ultrathon™ was as effective as 75% DEET, providing up to 12 hours of greater than 95% protection against mosquito bites. Sawyer Products makes a controlled-release 20% DEET lotion, which traps the chemical in a protein particle that slowly releases it to the skin surface. This formulation provides a repellency equivalent to a standard 50% DEET preparation, lasting about 5 hours. Products with 5–35% DEET provide adequate protection under most conditions. However, the American Academy of Pediatrics recommends that DEET-containing repellents used on children should not contain more than 10% DEET. In addition, DEET containing insect repellants exhibit most of the drawbacks of chemical insect repellants discussed above.

Young children should not apply DEET-containing repellents themselves, to minimize the possibility of irritation of eyes or mucous membranes. Inadvertent exposure of such tissues to higher concentrations of DEET may result in pain, watering of the eyes, and general tissue irritation. For the same reasons, DEET should not be applied to a child's hands. To prevent irritation after the repellent is applied, it should be wiped from the palm surfaces to prevent inadvertent contact with the eyes, mouth, and genitals. The repellents should never be used on cuts, wounds, and inflamed, irritated, or eczematous skin. Aerosol formulations should not be inhaled or sprayed into the eyes. Contact with plastics (e.g., watch crystals, eyeglass frames), rayon, spandex, and painted or varnished surfaces should be avoided because DEET can damage those surfaces. Once indoors, the repellent-treated areas should be washed with soap and water. Washing the repellent from the skin surface is particularly important under circumstances where a repellent is likely to be applied for several consecutive days.

Repellents containing DEET must be carefully applied because they can damage plastics (such as watch crystals and eyeglasses frames), rayon, spandex, other synthetic fabrics, leather, and painted or varnished surfaces. DEET does not damage natural fibers, such as cotton or wool, and has no effect on nylon. There are many accounts of the unpleasant odor or greasy feel of DEET.

In children, concentrations greater than 10% of DEET, too frequent applications, and oral ingestion are associated with toxicity, including encephalopathy and seizures. Deaths have been documented in relation to improper exposure to DEET. DEET is not recommended for infants less than two month of age.

IR3535

IR3535 (3-[N-butyl-N-acetyl]-aminopropionic acid) is a chemical repellent that has been available in Europe for 20 years and has been sold in the United States since 1999. This repellent (at 7.5%) is currently available through the Avon Corporation as Skin-So-Soft Bug Guard Plus IR3535. IR3535 is structurally similar to the amino acid alanine, and the EPA classifies it as a biopesticide. It is labeled for use against mosquitoes, ticks, and biting flies. In a recent laboratory comparative study of the efficacy of insect repellents to prevent mosquito bites, Avon Corporation's IR3535-based repellent provided an average complete protection time of only about 23 minutes (range, 10–60 min) (Fradin, 2002).

Piperidine

Although not yet for sale in the United States, a piperidine-based repellent is sold in Europe as Autan Bayrepel. Derived from pepper, this repellent is labeled for use against ticks, mosquitoes, and flies. The manufacturer claims DEET-like efficacy against mosquitoes, lasting as few as 2 hr and sometimes as long as 8 hours, depending on the species.

Skin-So-Soft Bath Oil

Avon Corporation's Skin-So-Soft bath oil received considerable media attention several years ago when some consumers reported it to be effective as a mosquito repellent. Studies have shown that Skin-So-Soft bath oil has a minimal repellent effect, and it is at least 10 times less effective than 12.5% DEET. The limited mosquito repellent effect of Skin-So-Soft oil may be due to its fragrance or to other components of its formulation, which may possess some repellent activity. The manufacturer has never marketed the bath oil as an insect repellent.

Thousands of plants have been tested as sources of insect repellents. Although none of the plant-derived chemicals tested to date demonstrate the broad effectiveness and duration of the protection of DEET, a few appear to show repellent activity.

Citronella

Marketed products containing citronella include Natrapel™, Buzz Away™, Herbal Armor™, and Green Ban™. Oil of citronella is a plant-derived ingredient found in many natural or herbal insect repellents marketed in the United States. Oil of citronella is extracted from the grass plants *Cymbopogon nardus* and *Cymbopogon winterianus*. Conflicting data exist on the efficacy of citronella-based products. This data variation may be attributed to differences in study methodology, location, and species of the biting insects tested. One comparative laboratory study demonstrated that marketed citronella-based insect repellents protected against mosquito bites for an average of less than 20 minutes. In general, citronella-based repellents provide considerably shorter protection than DEET repellents. Therefore, they require more frequent reapplication to maintain their effectiveness. For maximum repellent effectiveness of these products, it is recommended to repeat applications at one-hour intervals.

Soybean Oil

This repellent may provide longer-lasting protection than citronella-based repellents. In some studies, one soybean oil product provided complete protection against mosquito bites for as long as 3.5 hours, and against blackflies for as long as 10 hours. However, the benefits of soybean oil as an insect repellent have not been extensively documented.

Eucalyptus

A derivative, p-menthane-3,8-diol (PMD), isolated from the oil of the lemon eucalyptus plant has shown promise as an insect repellent. A 30% PMD preparation appears to provide protection comparable to 20% DEET but requires more frequent reapplication to maintain the same level of protection. PMD-based repellents show low toxicity, but care must be taken to keep them out of the eyes because PMD can cause significant eye irritation.

A search for the perfect topical insect repellent has continued. The ideal agent would remain effective for at least 8 hours and have no toxic side effects. No available topical insect repellent meets those criteria.

There remains a need for an oral inhibitor of biting insects that would fulfill all of the criteria listed in Paragraph 0011 above. Such an agent would inhibit multiple species of biting arthropods, including but not limited to mosquitoes, remain effective for at least 8 hours, cause no irritation to the skin or mucous membranes, cause no systemic toxicity especially in children, be resistant to being rubbed or washed off and not have an unpleasant taste or smell.

SUMMARY

Certain embodiments of the present invention concern compositions and/or methods of producing and using biting insect inhibitors derived from naturally occurring products. In one aspect, an insect inhibitor composition suitable for human oral and/or topical application comprises one or more vitamins combined with one or more herbs. It will be understood that where the present disclosure refer to a composition comprising one or more herbs, the one or more herbs may be present in any form, including but not limited to the native herb, a crushed herb, an extract, a concentrate, a decoction, an infusion, a homogenate, an essence and/or a distillate of an herb.

In various embodiments, the compositions inhibit insects from biting subjects following oral ingestion of the compositions by the subjects. In other embodiments, the compositions reduce inflammation, swelling, redness and/or itching of the localized region of an insect bite. The compositions may be provided in any form known in the art, but in a preferred embodiment come in the form of a water-based solution suitable for administration with a spray bottle, for example by spraying into the mouth of a subject, followed by ingestion.

In another preferred embodiment, a composition suitable for human oral and/or external application comprises one or more vitamins combined with one or more herbs to inhibit mosquitoes from biting subjects.

A composition suitable for oral and/or external application may be provided in a variety of forms, including but not limited to a dilute liquid, a concentrated liquid, a more concentrated cream, a paste or a hydratable dry composition. Other possible forms may be solutions, lotions, creams, gels, aerosol and pump sprays, and impregnated towelettes. The composition may contain a variety of levels of the individual components. For example, a single application amount of the individual components of the composition may be determined. This amount may be administered as a single application or may be divided into multiple smaller applications dependent on the insect exposure and the individual. Where the composition is a liquid for oral application, for example, one squirt of a standard spray applicator may constitute one-fifth of a predetermined amount of the individual components, making five squirts the suitable application for an adult individual prior to insect exposure. Although dosage may vary, in certain embodiments a one fluid ounce spray applicator may contain enough liquid for about 250 sprays, making a 5-spray application about 1/50 of a fluid ounce.

The effective dosage of composition will depend upon a variety of factors known in the art, such as the body mass of the individual to whom the composition is administered, the relative sensitivities of different target insects to the composition and the length of exposure to insects. Where prolonged exposure may result in a decrease in efficacy, a repeated administration may be used.

Certain embodiments concern methods to minimize, inhibit and/or prevent insect bites. Other embodiments concern methods to treat a subject bitten by an insect. Such methods may comprise administering a composition suitable for oral and/or external application that includes at least one herbal compound combined with at least one vitamin compound. The composition may be administered in various forms as mentioned above. The amount of the individual components of the composition may be adjusted to provide an optimum insect inhibiting formulation, including a predetermined beneficial amount, such as several sprays for an adult subject and fewer for a young subject (e.g. an infant or child). The skilled artisan will realize that the disclosed methods include, but are not limited to administration to human subjects. However, subjects of interest may include humans, cats, dogs, horses, cows, goats, pigs, mammals and vertebrates in general. Where oral spray administration is inappropriate for administering to a particular species of mammal, alternative delivery methods may be utilized. For example, a standard dosage may be determined and mixed with a water and/or food supply for a subject animal. The skilled artisan will realize that with such administration the absorption of the composition may be affected by the type and/or amount of liquid or food ingested and dosages may be adjusted appropriately to compensate for reduced absorption.

In various embodiments, methods to treat subjects for insect bites may comprise oral and/or topical administration of a composition comprising at least one vitamin and at least one herb. The administration may be used to reduce, inhibit or eliminate localized swelling, itching, inflammation, redness and other reactions to insect bites.

DETAILED DESCRIPTION

Definitions

As used herein, the term "about" means plus or minus 15 percent of an amount. For example, "about 100" would mean a value between 85 and 115. As used herein, the terms "a", "an" and "the" may refer to one or more than one of an item. The terms "and" and "or" may be used in the conjunctive or disjunctive and will generally be understood to be equivalent to "and/or".

As used herein, an "inhibitor" of biting insects or "biting insect inhibitor" refers to a composition that reduces the number of insect bites suffered by a subject after administration of the composition, in comparison to a control subject exposed to insects under identical circumstances without administration of the composition. It will be understood that an "inhibitor" of biting insects may or may not also repel insects, that is prevent insects from landing on a subject. In preferred embodiments, the composition is effective to completely inhibit biting insects, i.e., the subject suffers no insect bites after administration of the composition. However, the skilled artisan will realize that efficacy of insect inhibitors may depend upon a variety of factors; such as the dosage of inhibitor administered, the route of administration (for example, oral or topical); the length of time following administration; the body mass of the subject; the number and species of biting insects present; and potentially environmental factors such as humidity, temperature, wind speed, sunlight or shade, etc.

Description

The following embodiments relate to compositions that, in one aspect, inhibit insects from biting subjects following oral administration to the subjects. The compositions provide prolonged protection of subjects against biting insects. The subjects may be adult subjects, juvenile subjects and/or infant subjects. Because the compositions exhibit little or no toxicity, they may be administered to infant subjects to protect against biting insects, unlike present commercial insect repellants that are not recommended for use with infants.

Plants whose essential oils reportedly have purported insect repellent activity include citronella, cedar, verbena, pennyroyal, geranium, lavender, pine, cajeput, cinnamon, rosemary, basil, thyme, allspice, garlic, and peppermint. Unlike synthetic insect repellents, plant-derived insect repellents have been poorly studied. When tested, most of the essential oils yield short-lasting protection, lasting from a few minutes to as long as 2 hours. The use of plant derived materials as inhibitors of insect biting remains uncharacterized to date.

Embodiments relate to compositions and the use of these compositions as agents for the prevention and/or treatment of insect bites. The compositions may include combinations or sub-combinations of components derived from one or more vitamins such as thiamin (B-1), riboflavin (B-2), niacin (B-3), pantothenic acid (B-5), pyridoxine (B-6), folic acid (B-9), cyanocobalamin (B-12), choline, inositol, d-biotin, para-aminobenzoic acid, lecithin and one or more herbs such as peppermint, barley grass, lobelia, chlorella, watercress, alfalfa, parsley and rice bran. In one embodiment, the composition may comprise a suitable amount of all the herbs and all the vitamins mentioned.

In one embodiment, the composition is administered to an individual in need of treatment to reduce inflammation (e.g. orally administered and/or externally applied to an insect bite). In another embodiment, the composition may be administered to an individual to inhibit biting insects. In still another embodiment, the compositions may be administered to maintain a continuous protection against biting insects for a prolonged period (e.g. approximately 8 hours).

The following information is presented as general background information relevant to various herbs and vitamins. The herbs discussed below have been reported to have effects as naturopathic and/or homeopathic remedies for a variety of conditions. The skilled artisan will realize that such naturopathic and/or homeopathic uses may or may not be relevant to the compositions and methods disclosed herein for inhibition of biting insects and/or inflammation caused by insect bites.

Herbs

Barley: *Hordeum distichon* (LINN.), *Hordeum vulgare* L.; Graminaceae

Action and Uses: Pearl Barley may be used for the preparation of a decoction which is a nutritive and demulcent drink in febrile conditions and in catarrhal affections of the respiratory and urinary organs. Barley water is used to dilute cows' milk for young infants, reportedly to prevent the formation of hard masses of curd in the stomach. Malt is produced from barley by a process of steeping and drying that develop a ferment 'diatase' needed for the production of alcoholic malt liquors, but in the form of Malt Extract it is largely used in homeopathic medicine. Vinegar is an acid liquid produced by oxidation of fermented malt wort. Malt vinegar is the only vinegar that has been used medicinally. The parts of the barley plant usually used include grain and germinated seeds (barley sprouts). Reported properties include demulcent, digestant, carminative, nutritive.

Uses: A mucilaginous substance is obtained when hulled barley (pearl barley) is cooked. It is thought to be a good nutritional source for throat or stomach problems. The demulcent properties of cooked barley may be useful in external treatment of sores, fevers, diarrhea, gout, and tumors. Used as a tonic during convalescence. Barley water is a skin freshener, cleanses and softens skin. Drinking barley water is reported to clear and beautify the skin; sweeten with honey and orange juice.

Nutrient Content: Iron, sulfur, phosphorus, magnesium, niacin, protein, vitamin B1. Barley shoots are reportedly used to dry breast milk, treat food stagnation, weak stomach, weak digestion, loss of appetite, and hepatitis.

Warning: Barley should be avoided by nursing mothers.

*Lobelia: Lobelia inflata* (LINN.) Family: N.O. Lobeliaceae

Action and Uses: Some reported uses are as an expectorant, diaphoretic, and anti-asthmatic. It should not be employed as an emetic. Some reports indicate value as an expectorant in bronchitis or as a counterirritant when combined with other ingredients in ointment form. It is sometimes given in convulsive and inflammatory disorders such as epilepsy, tetanus, diphtheria and tonsilitis. It may also be used for relaxation purposes. It may also be used as an enema.

Externally, an infusion has been found useful in ophthalmia, and an ointment may be used as a local application for sprains, bruises, or skin diseases, alone, or in powder combined with other components. The oil of *Lobelia* is reportedly of use in treating tetanus. The oil may be useful as an expectorant, nauseant, sedative, and diaphoretic, when given every one or two hours. In excessive doses the effects may include depression, nausea, cold-sweats, and possibly death.

Other Species—*L. Dortmanna* is indigenous to Great Britain, and is similar in action to *L. inflata*. A dose of the fresh plant reportedly cures headaches and noises in the ears. *L. Erinus*. A dose of the plant has reportedly been used in cancer and has produced pain relief. It has also been used as to treat syphilis. LOBELIA, BLUE (*L. Syphilitica*) and LOBELIA RED (*L. Cardinalia*). Both of these are used in homeopathy. The first is diaphoretic, emetic and cathartic and has been used in dropsy, diarrhea, syphilis and dysentery, the root being the part used. The Red *Lobelia* is said to be anthelmintic, nervine and antispasmodic. *L. Kalmit.* is said to be used by the Indians in the cure of syphilis. *L. purpurascens*. also has reported homeopathic medicinal uses.

Watercress: *Nasturtium officinale*. Family: N.O. Cruciferae

Action and Uses: Watercress is reportedly of use for its antiscorbutic qualities and has been used as such from the earliest times. As a salad it supposedly promotes appetite. Watercress has also reportedly been used in tuberculosis. Its active components are said to be at their best when the plant is flowering. Reported properties include diuretic, expectorant, purgative, stimulant, stomach aid, and tonic.

Reportedly good for urinary bladder problems. Promotes kidney function and relieves fluid retention. Relieves indigestion and stops gas formation. Stimulates rate of metabolism and is taken as a spring tonic. Watercress has reportedly been recommended for use against gout, scurvy, mild digestive disturbances, anemia, and catarrh of the upper respiratory tract. Reportedly effective as an expectorant, it is also beneficial for tuberculosis, scurvy, anemia, and eczema. Its high vitamin C content makes it a good general preventative. Used as a post-partum (after childbirth) remedy to prevent infections. Having a slight iodine content, watercress is a dietary remedy for thyroid problems. In addition, the richness of its mineral, iron and iodine content stimulates glandular activity. Limited loss of hair caused by a fungus may be treated by an application of watercress juice. Leaf extracts are used clinically in India to correct vitamin deficiency.

Dosage: As an expressed juice; 1 to 2 fluid ounces.

Nutrient Content: Iodine, niacin, magnesium, manganese, phosphorus, sodium, iron, calcium, vitamins A, B1, B2, C, E and zinc.

Warning: Do not harvest leaves from polluted waters. Poisonings have resulted from eating leaves from plants growing in polluted waters, from which the plant has absorbed heavy metals and toxins. Excessive or prolonged use can lead to stomach upset and kidney problems. It should not be taken daily and no longer than 4 weeks even with interruptions. The juice should not be taken undiluted, because it can produce inflammations in the throat and stomach. Some doctors caution against use during pregnancy.

Parsley: *Carum petroselinum* (BENTH.) Family: N.O. Umbelliferae

Action and Uses: The leaves are extensively cultivated, not only for use fresh, but also for the purpose of being dried and powdered. In addition to the leaves, the stems are also dried and powdered. The roots of the turnip-rooted variety are used as a vegetable and flavoring. Two-year-old roots and dried leaves are employed for making Parsley Tea. The seeds are used for the extraction of an oil called Apiol. The best kind of seed for homeopathic or naturopathic medicinal purposes is that obtained from the Triple Moss curled variety.

The oleoresin of parsley has been reported to influence nerve centers of the head and spine, and in large doses may produces giddiness and deafness, decreased blood-pressure and slowing of the pulse and possibly paralysis. Parsley is reportedly used chiefly for its diuretic properties, a strong decoction of the root being used to treat the kidneys, (dropsy and jaundice). The dried leaves are also used for the same purpose.

A report in France indicated a popular remedy for scrofulous swellings is green Parsley and snails, pounded in a mortar to an ointment, spread on linen and applied daily. The bruised leaves, applied externally, have been used in a similar manner as Violet leaves (also Celandine, Clover and Comfrey), to treat tumors suspected to be of a pre-cancerous nature. It is also reported that this may be a remedy for the bites and stings of poisonous insects.

Peppermint: *Mentha piperita* (SM.). Family: N.O. Labiatae. Synonym—Brandy Mint.

Action and Uses: The parts of the herb used include the leaves, oil and flowering tops. Peppermint oil is the most extensively used of all the volatile oils. The anti-spasmodic action of the volatile oil is more marked than in any other oil, and is reported to relieve pains arising in the alimentary canal.

From its stimulating, stomachic and carminative properties, it is used in certain forms of dyspepsia, being mostly used for flatulence and colic. It may also be employed for other sudden pains and for cramp in the abdomen. Wide use has been made of Peppermint in cholera and diarrhea. May be used for chills, colic, fever, nausea, diarrhea, heart trouble, rheumatism, convulsions, spasms, dizziness, vomiting, travel sickness, dysentery, cholera, dysmenorrhea, palpitations of the heart, the grippe, hysteria, insomnia, neuralgia, and also reportedly used for headaches. Used for colds, flu, sore throat, laryngitis, gas and mild digestive disorders. The leaves can be made into a salve or a bath additive for itching skin conditions. Extracts have been used against herpes simplex, Newcastle disease, and other viruses. The oil reportedly stops spasms of smooth muscles. Externally, peppermint helps rheumatism, neuralgia, and headaches (e.g., migraines).

Reportedly, it is generally combined with other medicines when its stomach aiding effects are required, being also employed with purgatives to prevent griping. Oil of Peppermint reportedly alleviates sickness and nausea, and is used to disguise the taste of unpalatable drugs, as it imparts its aromatic characteristics to whatever prescription it enters into. It is also reportedly used as an infants' cordial. The oil itself is often combined with sugar and added to pills, also a spirit made from the oil, but the preparation in most general use is Peppermint Water, which is the oil and water distilled together.

Peppermint is reportedly used to assist in raising internal heat and inducing perspiration, although its strength is soon exhausted. In slight colds or early indications of disease, a free use of Peppermint tea may treat the disease onset. Peppermint tea is used also for palpitation of the heart. In cases of hysteria and nervous disorders, Peppermint was reported to be augmented by the addition of equal quantities of Wood Betony.

A single cup of peppermint tea, drunk in sips and as warm as possible, may be of use to treat for example queasiness, nausea, a feeling of fullness, or severe vomiting. Peppermint tea promotes bile flow, improves bile production in the liver, and also exercises a positive influence on pancreatic function. But, avoid peppermint if internal ulcers are present.

Warning: May interfere with iron absorption. Oil is toxic if taken internally in large doses; may cause dermatitis. Menthol, the major chemical component of peppermint oil, may cause allergic reactions. Avoid prolonged use of the essential oil as an inhalant. Mint should not be given to children for more than a week at a time without a break. It is advised not to give any form of mint directly to young babies. Also, peppermint may reduce milk flow if breast-feeding.

Alfalfa: *Medicago sativa* L. Leguminosae

Uses: Alfalfa tea is commonly used as a beverage. Nutritious fresh or dried leaf tea is reportedly used to promote appetite, for weight gain, as a diuretic, and reportedly stops bleeding. It is a source of commercial chlorophyll and carotene. It also contains the anti-oxidant tricin. Alfalfa has anti-fungal, and setrogenic activity. Unsubstantiated claims include use for cancer, diabetes, alcoholism, arthritis, etc. It is high in chlorophyll and nutrients. It is reported to alkalinize the body, as well as detoxify the body, especially the liver. It is reportedly used for colon disorders, anemia, hemorrhaging, indigestion, vitamin or mineral deficiency, laxative, cystitis, blood purifier, gas, edema, diabetes, ulcers, and arthritis. It may promote pituitary gland function. Effects include alterative, antipyretic, diuretic, appetite stimulant and hemostatic effects.

Nutrient Content: It contains biotin, calcium, choline, inositol, iron, magnesium, PABA, phosphorus, potassium, protein, sodium, sulfur, tryptophan (amino acid), and vitamins A, B complex, C, D, E, K, P, and U.

Warning: Alfalfa has been reported to aggravate lupus and other auto-immune disorders. Avoid alfalfa if an auto-immune problem exists. Consuming large quantities of Alfalfa saponins may cause breakdown of red blood cells, causing bloating in livestock (thus weight gain). Recent reports suggest that Alfalfa sprouts (or the canavanine, especially in the seeds), may be associated with lupus (systemic lupus erythematosus), causing recurrence in patients in which the disease had become dormant.

Rice Bran

Rice bran is a by-product of the milling of rice. It consists mostly of the bran layer and germ of the rice with some fragments of hull and broken rice. The calcium level in rice bran will vary with the amount of added calcium carbonate. When the amount of added calcium carbonate exceeds 3 percent (total calcium exceeds 1.2 percent), then the percentage of calcium carbonate must be stated in the product name. Rice bran is similar to oats in crude protein, fat, fiber and energy.

Rice Bran is a source of original B-complex in the outer layers of the rice grain. Vitamin B-complex is a source for strong, steady nerves and sustained energy. The B-complex has been reportedly used for cessation from aggravation. Rice Bran, being a very rich source of a balanced B-complex profile of vitamins, can be used to maintain normal blood sugar levels for those suffering from low blood sugar.

Chlorella

A genus of unicellular green algae, potentially a source of high-grade protein and B-complex vitamins. Any alga of the genus *Chlorella*. The name *Chlorella* derives from the Latin words meaning 'leaf' (green) and 'small', referring to the unusually high content of chlorophyll (the highest of any known plant) that gives *Chlorella* its characteristic deep emerald-green color. This particular fresh-water, single celled microscopic plant contains a host of nutrients. In addition to chlorophyll it contains vitamins, minerals, dietary fiber, nucleic acids, amino acids, enzymes, CGF (*Chlorella* Growth Factor) and other substances. Under favorable growth conditions of strong sunlight, pure water and clean air, *Chlorella* multiplies at an incredible rate, the complete reproduction cycle taking less than 24 hours.

There are over 70,000 species of algae in the world. *Chlorella Pyrensoida* is one of the most common species found in watersheds. *Chlorella* contains the full Vitamin B Complex, Vitamins E & C and has a wide range of minerals, including magnesium, potassium, iron and calcium.

Uses. Reportedly of use for treatment of cancer. May increase production of T-cells and macrophages with activity against cancer. *Chlorella* has reportedly been shown to promote the production of interferon (IFN), which stimulates macrophage production. Chlorella may stimulate the activity of T-cells and macrophages by increasing IFN levels thus enhancing the immune system's ability to combat infection, cancer and other diseases.

*Chlorella* has the highest amounts of chlorophyll of any plant known. Chlorophyll is structurally similar to hemoglobin (found in red blood cells) except for containing magnesium instead of iron. Magnesium is essential for the heart to function properly. Chlorophyll has reportedly been used in the treatment of cardiac hypertension. Chlorophyll has also been used to treat anemia and reportedly stimulates the production of red blood cells in the body.

When eaten, *Chlorella* reportedly causes beneficial stomach bacteria (Lactobacillus) to multiply at four times the normal rate. This improves digestion and thus the body's ability to absorb nutrients.

*Chlorella* includes a fibrous, indigestible outer shell (20%) and inner nutrients (80%). It is the fibrous material that has been reported to bind with heavy metals and other toxins that may accumulate in the bodies. It is reported that a period of 3–6 months consumption of *Chlorella* may result in elimination of heavy metals and other toxins. Use of up to 15–20 grams of *Chlorella* per day has been reported.

*Chlorella* has been used for treatment of Alzheimer's Dementia and Attention Deficit Disorder. Alzheimer's patients have been demonstrated to have high levels of aluminum in their brains. *Chlorella* may assist in elimination of aluminum and may also improve oxygen transfer capabilities, aiding alertness and mental focus.

*Chlorella* has the ability to quadruple in quantity every 20 hours, which is an extraordinarily high growth rate. Exactly what CGF (*Chorella* growth factor) is remains a mystery. CGF has hormone-like qualities and appears to stimulate tissue repair. *Chlorella* has been used as a topical treatment for damaged tissue.

Poor diet, for example the consumption of excess carbonated soft drinks and processed sugars, may result in blood acidification. *Chlorella* is alkaline in nature any may help balance this acidity to maintain a neutral blood pH, optimally 7.4. *Chlorella* has a number of properties which are helpful to organs and tissues that have been injured by a variety of causes. It has been reported to promote liver health. Although some positive effects of taking *Chlorella* may be felt immediately, such as correcting constipation and bad breath, *Chlorella*'s full nutritive and detoxifying capabilities often take 3–6 months to be fully appreciated. *Chlorella* belongs to a small group of foods that have been called Nutriceuticals.

Both Watershed *Chlorella* and Watershed *spirulina* are particular strains of algae. Watershed *Chlorella* is a strain of algae known as *Chlorella Pyrensoida*. From a single pure source, this algae has been reproduced for thousands of generations. Control of the genetic purity of Watershed *Chlorella* may provide beneficial effects on its nutritional and nutriceutical properties.

It has been reported that mice injected with cancer cells showed a higher resistance to this challenge if they had been fed *Chlorella*. Other tests reported that *Chlorella* growth factor improves resistance to abdominal tumors while increasing the number of immune cells in the abdominal cavity. *Chlorella* promotes cell reproduction, reduces cholesterol and increases hemoglobin levels. Because of its broad nutritional and detoxifying profile, *Chlorella* promotes the repair of bodily organs and tissues that have been injured or otherwise damaged.

Numerous research projects in the USA and Europe indicate that *Chlorella* can also aid the body in the breakdown of persistent hydrocarbon and metallic toxins such as DDT, PCB, mercury, cadmium and lead, while strengthening the immune system response. In Japan, interest in *Chlorella* has focused largely on its detoxifying properties, its ability to neutralize or remove poisonous substances from the body. The fibrous materials in *Chlorella* also improve digestion and promote the growth of beneficial aerobic bacteria in the stomach.

Analysis shows that *Chlorella Pyrensoidosa* contains a comparable variety of minerals, vitamins and amino acids to other algae: Sporopollenin, which is only present in *Chlorella Pyrensoida*, acts in the same detoxifying way. *Chlorella*'s indigestible cell wall needs to be ruptured to allow access to its nutrients and a variety of methods are used, some of which damage the nutrients.

The method used herein by the *Chlorella* producer (TCMC) ensures the highest quality, which is confirmed by an annual independent analysis by the Japan Food Research Laboratory. Japan is the only country that has strict standards and importation controls over heavy metals and bacterial content in *Chlorella*. The digestibility of the *Chlorella* used is confirmed by the Japan Government's Ministry of Health to be between 76% and 79%, the highest on the market. *Chlorella* was analyzed by Dr L. Lewis, Doctor of Physiology at Duke University in 1992. Using a Scanning Electron Microscope (SEM), two samples of *Chlorella* were examined, the source used herein and a competitor's brand. Both were deemed to be free of contamination, however, the source of *Chlorella* used herein was the only one found to have a disrupted cell wall by SEM examination.

Additive: Potassium Sorbate

In certain embodiments, a preservative may be added to a composition of insect inhibitor to prevent growth of microorganisms and/or to maintain freshness. One example of a preservative is potassium sorbate.

Potassium sorbate is a potassium salt of sorbic acid, a polyunsaturated fat used to inhibit mold growth. Sorbic acid was first isolated from the oil of the unripened rowan berry (sorbapple or mountain ash berry) in 1959 by A. W. Hoffmann. Sorbic acid obtained its name from the scientific name for mountain ash (i.e. *Sorbus aucuparia*, Linne), the parent of the rowan berry. The value of sorbic acid, or its salts, was not immediately recognized. It was only much later that these compounds were appreciated for their ability to interfere with ATP metabolism in microbes, while posing no health risk when consumed by mammals. Sorbic acid is one of the most thoroughly tested food additives in history. It has been found to be non-toxic even when taken in large quantities, and breaks down in the body into water and carbon dioxide in the Kreb Cycle.

Herbal therapies may be considered a form of combination therapy. The collective effect of these agents typically results in reduced toxicity, and appearance of new and novel activities.

Vitamins

In various embodiments, the compositions disclosed herein comprise one or more vitamins. The following discussion provides general background information on vitamins.

Choline

Reportedly important in controlling fat and cholesterol buildup in the body; prevents fat from accumulating in the liver; facilitates the movement of fats in the cells; helps regulate the kidneys, liver and gallbladder; important for nerve transmission; helps improve memory.

Deficiency Symptoms: Reportedly a deficiency may result in cirrhosis and fatty degeneration of the liver, hardening of the arteries, heart problems, high blood pressure and hemorrhaging kidneys. Choline reportedly assists in controlling weight as well as cholesterol levels, keeping cell membranes healthy and in preventing gallstones. It is thought to be useful in the maintenance of the nervous system, assisting memory and learning, and may help to fight infections, including hepatitis and AIDS. Choline is reportedly needed for normal membrane structure and function.

Choline is the major precursor of betaine, and it is used by the kidneys to maintain water balance and by the liver as a source of methyl-groups for methionine formation. It is also used to produce the important neurotransmitter acetylcholine. It assists in nerve impulse transmission, gallbladder regulation, liver functions and lecithin production.

A deficiency of choline does not happen easily but if it is deficient it may lead to liver disease, raised cholesterol levels, high blood pressure as well as kidney problems. Choline deficiency may also manifest itself in the inability to digest fats, stunted growth and fatty buildup in the liver. Memory and brain function may also be impaired.

Dosage: The dosage indicated is the Recommended Dietary Allowance (RDA), but is the minimum required per day, to ward off serious deficiency of this particular nutrient. In the therapeutic use of this nutrient, the dosage is usually increased considerably, but the toxicity level must be kept in mind. The dosage is relative to the amount of fats ingested in the diet, but for a guide: male 550 mg/per day and female 425 mg per day, although mega dose vitamin proponents use far higher dosages. More choline may be required during alcohol consumption, refined sugar consumption or taking large amounts of nicotinic acid.

Toxicity and Symptoms of High Intake: The maximum level of choline has been set for safety at 3.5 g/day. Taking too much choline could result in nausea, depression, and could trigger existing epilepsy. Hypotension, sweating, salivation and diarrhea have also been reported. Choline is recommended in the same dose as inositol and together with the B group vitamins as well as vitamin A and linoleic acid.

Vitamin B-1 (Thiamin)

Vitamin B-1 reportedly plays a role in the body's metabolic cycle for generating energy, aids in the digestion of carbohydrates and is important for the normal functioning of the nervous system, muscles and heart. It also stabilizes the appetite, promotes growth and good muscle tone.

Deficiency Symptoms: May lead to the loss of appetite, weakness and feeling tired, paralysis and nervous irritability, insomnia, loss of weight, aches and pains, mental depression and constipation, heart and gastrointestinal problems.

Vitamin B1 reportedly is used in many different body functions and deficiencies may have far reaching effects on the body. Yet very little of this vitamin is stored in the body, and depletion of this vitamin can happen within 14 days. Thiamin is also an essential nutrient, somebody suffering from beriberi, scarcely able to lift their head from their pillow, will respond quickly from injected thiamin, and will be on their feet within a matter of hours.

Vitamin B1 may enhance circulation, help with blood formation and the metabolism of carbohydrates. It is also needed for the health of the nervous system and is used in the biosynthesis of a number of cell constituents, including the neurotransmitter acetylcholine and gamma-aminobutyric acid (GABA). It is used in the manufacture of hydrochloric acid, and therefore plays a part in digestion.

It is also good for the brain and may help with depression and assist with memory and learning. In children it is required for growth and additionally it has shown some indication to alleviate arthritis, cataracts and aid in infertility.

Dosage: The Recommended Dietary Allowance (RDA) is the minimum required per day to ward off serious deficiency of this particular nutrient. In the therapeutic use of this nutrient, the dosage is usually increased considerably, but the toxicity level must be kept in mind. For males: 1.4 mg per day and females: 1.0 mg per day, although 50 mg is usually used in supplementation.

Inositol

Necessary for the formation of lecithin; aids in the breakdown of fats; helps reduce blood cholesterol; helps prevent thinning hair.

Deficiency Symptoms: May result in high blood cholesterol, constipation, eczema, or hair loss. Inositol is needed for health at the cellular level and a fair concentration is found in the lens of the human eye as well as the heart. Inositol plays an important part in the health of cell membranes especially the specialized cells in the brain, bone marrow, eyes and intestines. Inositol is said to promote healthy hair, hair growth, and helps in controlling estrogen levels and may assist in preventing breast lumps. It may also be of benefit in reducing blood cholesterol levels.

Dosage: The RDA is the minimum required to ward off serious deficiency of this particular nutrient. In the therapeutic use of this nutrient, the dosage is usually increased considerably, but the toxicity level must be kept in mind. Supplementation is usually 100 mg per day Toxicity and Symptoms of High Intake: No toxic effects known, but diarrhea has been noted with the intake of very high dosage of inositol.

Folic Acid (Vitamin B-9)

Folic acid, also known as Vitamin B9, is also referred to as folacin or folate. This vitamin can be manufactured by the body and stored in the liver. It is needed for DNA and RNA synthesis, essential to the formation of red blood cells by its action on the bone marrow; aids in amino acid metabolism.

Deficiency Symptoms: A deficiency of folic acid in an unborn baby may increase the risk of the baby being born with spina bifida and other serious defects of the nervous system. Deficiency of folic acid may lead to fatigue, acne, a sore tongue, cracking at the corners the mouth (same as deficiency of vitamin B2, vitamin B6 as well as iron). Long term deficiency may result in anemia and later in osteoporosis, as well as cancer of the bowel and cervix.

Folic acid is reportedly needed for DNA synthesis and cell growth and is important for red blood cell formation, energy production as well as the forming of amino acids. Folic acid is essential for creating heme, the iron containing substance in hemoglobin, crucial for oxygen transport. It is important for cell division and replication. It is also required for protein metabolism and in treating folic acid anemia. This nutrient may be effective in treating depression and anxiety. Folic acid is reportedly very important in the development of the nervous system of a developing fetus.

Dosage: The dosage (400 micrograms per day) is the Recommended Dietary Allowance (RDA). In the therapeutic use of this nutrient, the dosage is usually increased considerably.

Pregnant women are sometimes advised to take a small supplement of folic acid to help prevent spina bifida and other congenial nervous disorders, and it may also reduce the risk of toxemia in pregnancy, premature labor and hemorrhaging. It is also thought to enhance the production of milk after delivery. Sufferers of psoriasis may consider taking extra folic acid, people under stress or anyone consuming alcohol. Women on birth control pills or hormone replacement therapy may benefit from folic acid. Light, heat and storage for extended periods can destroy this vitamin. Localized deficiencies may exist for smokers, as low levels have been detected in the lungs of smokers.

Toxicity and Symptoms of High Intake: Those on medication for epilepsy should be careful with large amounts of folic acid, since it can change the functioning of such drugs. Too much folic acid may mask a Vitamin B12 deficiency. Regular high intake of folic acid may cause digestive upset, energy loss and insomnia. Folic acid is more effective when taken with the B group vitamins—especially vitamin B12 and vitamin B6. Vitamin C is also recommended.

Vitamin B5—Pantothenic Acid

Participates in the release of energy from carbohydrates, fats and protein, aids in the utilization of vitamins; improves the body's resistance to stress; helps in cell building and the development of the central nervous system; helps the adrenal glands, fights infections by building antibodies.

Deficiency Symptoms: May lead to skin abnormalities, retarded growth, dizzy spells, digestive disturbances, vomiting, restlessness, stomach stress, muscle cramps. Consequences of low levels include frequent infection, fatigue, abdominal pains, sleep disturbances and neurological disorders including numbness, paresthesia (abnormal sensation such as "burning feet" syndrome), muscle weakness and cramps are also possible indications that this nutrient is in short supply.

Vitamin B5 plays an important role in the secretion of hormones, such as cortisone. Pantothenic acid is also used in the release of energy as well as the metabolism of fat, protein and carbohydrates. It is used in the creation of lipids, neurotransmitters, steroid hormones and hemoglobin.

Dosage: Recommended dosage of 10–100 mg is indicated.

Toxicity and Symptoms of High Intake: Pantothenic acid does not appear to be toxic in high dosage, although diarrhea, digestive disturbances and water retention have been reported on dosage exceeding 10 g a day.

Vitamin B-2 (Riboflavin)

Necessary for carbohydrate, fat and protein metabolism; aids in the formation of antibodies and red blood cells;

maintains cell respiration; needed for the maintenance of good vision, skin, nails & hair; alleviates eye fatigue; promotes general health.

Riboflavin is manufactured in the body by the intestinal flora and is easily absorbed, although very small quantities are stored, so there is a constant need for this vitamin. It is required by the body to use oxygen and for the metabolism of amino acids, fatty acids, and carbohydrates. Riboflavin is further needed to activate vitamin B6 (pyridoxine), helps to create niacin and assists the adrenal gland. It may be used for red blood cell formation, antibody production, cell respiration, and growth.

It eases watery eye fatigue and may be helpful in the prevention and treatment of cataracts. Vitamin B2 is required for the health of the mucus membranes in the digestive tract and helps with the absorption of iron and vitamin B6. Although it is needed for periods of rapid growth, it is also needed when protein intake is high.

Deficiency Symptoms: May result in itching and burning eyes; cracks and sores in the mouth and lips; bloodshot eyes; purplish tongue; dermatitis; retarded growth; digestive disturbances; trembling; and sluggishness. A shortage of this vitamin may manifest itself as eye disorders, inflammation of the mouth and tongue, and skin lesions. Dermatitis, dizziness, hair loss, insomnia, light sensitivity, poor digestion, retarded growth, and slow mental responses have also been reported. Burning feet can also be indicative of a shortage of B2.

Dosage: The RDA is the minimum that required per day to ward off serious deficiency of this particular nutrient. In the therapeutic use of this nutrient, the dosage is usually increased considerably, but the toxicity level must be kept in mind. Male 1.6 mg per day and female 1.2 mg per day although 50 mg is mostly recommended for supplementation. Extra dosage might be needed when consuming alcohol, antibiotics, and birth control pills or doing strenuous exercise, under stress or on a calorie-restricted diet.

Toxicity and Symptoms of High Intake: The limited capacity to absorb orally administered riboflavin precludes its potential for harm. Riboflavin intake of many times the RDA is without demonstrable toxicity. A yellow discoloration of the urine is seen with an increased intake of this vitamin.

Niacinamide (Niacin—Vitamin B-3)

Niacin is derived from two compounds—nicotinic acid and niacinamide. It improves circulation and reduces the cholesterol level in the blood; maintains the nervous system; helps metabolize protein, sugar and fat; reduces high blood pressure; increases energy through proper utilization of food; prevents pellagra; helps maintain a healthy skin, tongue and digestive system.

Vitamin B3 is required for cell respiration, helps in the release of energy and metabolism of carbohydrates, fats, and proteins, proper circulation and healthy skin, functioning of the nervous system, and normal secretion of bile and stomach fluids. It is used in the synthesis of sex hormones, treating schizophrenia and other mental illnesses, and as a memory-enhancer.

Nicotinic acid (but not nicotinamide) given in drug dosage reportedly improves the blood cholesterol profile, and has been used to clear the body of organic poisons, such as certain insecticides. People report more mental alertness when this vitamin is in sufficient supply. Niacin is best taken with the B group vitamins and vitamin C.

Deficiency Symptoms: May result in pellagra, gastrointestinal disturbance, nervousness, headaches, fatigue, mental depression, vague aches and pains, irritability, loss of appetite, insomnia, skin disorders, muscular weakness, indigestion, and canker sores.

Dosage: The RDA is the minimum that required per day to ward off serious deficiency of this particular nutrient. In the therapeutic use of this nutrient, the dosage is usually increased considerably, but the toxicity level must be kept in mind. Male 18 mg per day and female 13 mg per day although 100 mg is mostly used in supplementation.

Large doses given to lower cholesterol may produce hyperuricemia, and hepatic abnormalities. These effects are reversed if the drug is reduced in amount or discontinued. People with diabetes, glaucoma, any liver disease or peptic ulcers should be careful of niacin supplementation. Your daily cup of coffee also provides about 3 milligrams of niacin Toxicity and Symptoms of High Intake: Nicotinic acid, but not nicotinamide in doses larger than 200 mg causes flushing by dilating the blood vessels, which can also cause the blood pressure to drop. These flushes are normally harmless. Large dosages can also cause itching, elevated blood glucose, peptic ulcers and liver damage.

Vitamin B-6 (Pyridoxine)

Necessary for the synthesis and breakdown of amino acids; aids in fat and carbohydrate metabolism; aids in the formation of antibodies; maintains the central nervous system; aids in the removal of excess fluid of premenstrual women; promotes healthy skin; reduces muscle spasms, leg cramps, hand numbness, nausea & stiffness of hands; helps maintain a proper balance of sodium & phosphorous in the body.

Pyridoxine is required for the balancing of hormonal changes in women as well as assisting the immune system and the growth of new cells. It is also used in the processing and metabolism of proteins, fats and carbohydrates. Pyridoxine reportedly may also be of benefit for children with learning difficulties, as well as assisting in the prevention of dandruff, eczema and psoriasis.

Pyridoxine should be taken together with the entire B group vitamins, and in supplementation the quantity of B6 should be nearly the same as B2, as the B2 is needed to activate the Pyridoxine. Vitamin C, magnesium, sodium, potassium, zinc, linoleic acid and fatty acids may also be used in combination.

Deficiency Symptoms: May result in nervousness, insomnia, skin eruptions, loss of muscular control, anemia, mouth disorders, muscular weakness, dermatitis, arm and leg cramps, loss of hair, slow learning, and water retention. Irritability, nervousness and insomnia as well as general weakness, skin changes such as dermatitis and acne as well as asthma and allergies might develop when pyridoxine is in short supply. Symptoms may include nails that are ridged, an inflamed tongue as well as changes to bones—which can include osteoporosis and arthritis. Kidney stones may also appear. Women in particular may suffer from premenstrual fluid retention, severe period pains, emotional PMS symptoms, premenstrual acne and nausea in early pregnancy. Mood swings, depression as well as loss of sexual drive is sometimes noted when pyridoxine is in short supply and the person is on hormone replacement therapy or on birth control pills. Symptoms will be very much like those of B2 and B3 deficiency. Vitamin B6 is needed by the body to manufacture its own B3 vitamin.

Dosage: The RDA is the minimum that required per day to ward off serious deficiency of this particular nutrient. In the therapeutic use of this nutrient, the dosage is usually increased considerably, but the toxicity level must be kept in mind. Males 2 mg per day and females 2 mg per day. More may be required if taking antidepressants, contraceptive pills or on hormone replacement therapy. As this vitamin is readily lost in the urine, it must be taken regularly to ensure an adequate amount in the body. A very high protein diet, alcohol use, or allergies to MSG (mono sodium glutamate) and/or tartrazine may also indicate a need for increased vitamin B6 intake.

Toxicity and Symptoms of High Intake: Supplementation should be controlled as extreme dosage, such as in excess of 2,000 mg per day, may cause neurological damage. People on medication for Parkinson's disease should be careful about taking Vitamin B6 as it can inactivate L-dopa. People taking pyridoxine late at night sometimes experience very vivid dreams.

Biotin

Aids in the utilization of protein, folic acid, Pantothenic acid, and Vitamin B-12. Biotin is used in cell growth, the production of fatty acids, metabolism of fats, and proteins. It plays a role in the Kreb cycle, which is the process in which energy is released from food. Biotin is also indicated for healthy hair and skin, sweat glands, nerve tissue, bone marrow, and assisting with muscle pain. Biotin also helps with the transfer of carbon dioxide. Biotin is useful for maintaining a steady blood sugar level.

Biotin should be taken with the B-group vitamins, but Vitamin C, Vitamin B5 (pantothenic acid), Vitamin B12 and sulfur are good adjuvants. Biotin is sometimes added to the diet of a patient suffering from alopecia, to help with severe hair loss.

Deficiency Symptoms: May lead to extreme exhaustion, drowsiness, muscle pain, loss of appetite, depression, grayish skin color. Although a shortage of Biotin is rare, it can happen and may result in dry scaly skin, fatigue, nausea and vomiting, mental depression as well as tongue inflammation and high cholesterol.

Dosage: Recommended dosage for adults 300 microgram (0.3 mg) per day and pregnant and lactating women 300 microgram (0.3 mg) per day. Bodybuilders and athletes consuming raw eggs should be careful of not running into a biotin shortage, since raw eggs contain avidin, which binds with the biotin, making it impossible absorb by the body. Long-term use of antibiotics may also decrease the availability of biotin.

Biotin is present in cheese, beef liver, cauliflower, eggs, mushrooms, chicken breasts, salmon, spinach, brewer's yeast, nuts and can be manufactured in the body should a small shortfall occur.

Toxicity and Symptoms of High Intake: No toxic levels are known, as excesses are easily lost in the urine and feces. No side effects are known.

Vitamin B-12 (Cyanocobalamin)

Helps in the formation and regeneration of red blood cells, thus helping prevent anemia; necessary for carbohydrate, fat and protein metabolism; maintains a healthy nervous system; promotes growth in children; increases energy; needed for calcium absorption.

This complex structured compound with its cobalt cofactor is needed in the body in very small amounts. Vitamin B12 is reportedly needed in the manufacture and maintenance of red blood cells. It reportedly stimulates appetite, promotes growth and release of energy. It is often used with older people to give an energy boost, assist in preventing mental deterioration and helps with thought processes. It may aid with clearing up infections and providing protection against allergies and cancer. This vitamin is also used in the metabolism of fats, proteins and carbohydrates.

Deficiency Symptoms: May lead to pernicious anemia, poor appetite, growth failure in children, tiredness, brain damage, nervousness, neuritis, degeneration of spinal cord, depression, lack of balance. Some symptoms of a deficiency include a sore tongue, weakness, fatigue, and weight loss, back pain and apathy. It may further result in loss of balance, decreased reflexes, tingling of the fingers, ringing in the ears etc. A deficiency may also result in the raising of the level of homocysteine in the blood which in high doses can be toxic to the brain, which may be involved in Alzheimer disease. Severe deficiency may result in pernicious anemia, also called Addisonian pernicious anemia. Another problem that appears in deficiency is the eroding of the myelin sheath—the fatty sheath of tissue, which insulates the nerve fibers.

Dosage: The RDA for males and females is 3 µg per day. People on strict vegetarian and macrobiotic diets are often deficient on Vitamin B12. Some individuals exhibit a deficiency in absorption of vitamin B12 from the intestinal tract, which can lead to pernicious (destructive) anemia. Alcohol consumption or regular use of laxatives or antacids may also result in low B12 levels. Older people may require higher levels of this vitamin as many people older than sixty have difficulty extracting the vitamin from ingested food.

Vitamin B12 is not manufactured by any plants, and is only found in animal products. Therefore, a deficiency may result from strict all-vegetable diets. Unlike other water-soluble vitamins, B12 needs some 3 hours to be absorbed where other B vitamins are absorbed nearly immediately.

Toxicity and Symptoms of High Intake: Toxicity not established but vitamin B12 injections may result in skin problems if in large excess, but will normalize once the injections are stopped.

PABA (Para Amino Benzoic Acid)

Aids beneficial bacteria in producing folic acid; aids in the formation of red blood cells; contains sun screening properties; aids in the assimilation of Pantothenic acid. Para-aminobenzoic acid is often thought of as only an ingredient used in sunscreens, while it is actually also a nutritional ingredient. Since it is a moiety of PGA, a form of folic acid, some health professionals do not consider it a vitamin, but only a B-complex factor.

PABA is used to improve protein use in the body, it assists in red blood cell formation as well as manufacturing folic acid in the intestines. Para-aminobenzoic acid is used in sunscreen preparations since it can help protect the skin against ultra-violet radiation.

People suffering from vitiligo, over-pigmentation of skin, or without pigment in some spots, have reported an improvement of the skin after more PABA was ingested. PABA also assists with breaking down of protein and maintaining intestinal flora.

Deficiency Symptoms: May cause extreme fatigue, eczema, irritability, nervousness, constipation, headaches, digestive disorders, or hair turning prematurely gray. When PABA is in short supply fatigue, irritability, and depression might manifest. Weeping eczema has also been noted in people with PABA deficiency as well as patchy areas on the skin.

Dosage: No recommended dosage but 50 mg per day is usually used in supplementation. Long term antibiotic use may require more PABA from the body, but PABA may interfere with the effectiveness of sulfa drugs.

Toxicity and Symptoms of High Intake: When higher than factor (SPF) 8 sunscreens are used, the manufacture of vitamin D in the body may be reduced. Nausea, skin rashes and vomiting might be indicative of PABA taken in excess. Excessive levels of PABA are stored in the body and may cause liver damage. A ban was placed on the sale of OTC supplements containing large single doses of PABA.

Lecithin

Lecithin contains Choline and Inositol that are reportedly essential for the breakdown of fats and cholesterol. It may prevent arterial congestion, help distribute bodyweight, increase immunity to virus infections, clean the liver and purify the kidneys.

Lecithin is a phospholipid. It is produced daily within the liver if the diet is adequate. It is needed by every cell in the body and largely makes up cell membranes, where it increases membrane fluidity. This makes it ideal in preventing arteriosclerosis and assisting in protecting against cardiovascular disease.

Lecithin protects cells from oxidation, and helps make up the protective sheaths surrounding the brain. Using lecithin can improve brain function and has also been known to promote energy. Lecithin aids in the absorption of thiamine by the liver and is needed to help repair the damage to the liver caused by alcoholism.

Although it is a fatty substance, it is also a fat emulsifier. Lecithin enables fats, such as cholesterol, to be dispersed in water and removed from the body. Hence, it also supports the circulatory system by preventing fatty buildup in the arteries and vital organs.

Oral Application

In preferred embodiments, the disclosed compositions are delivered by oral administration. Oral spray is approximately five times faster and more efficient than capsules, pills or tablets. Intra-oral sprays are one of the fastest ways to deliver any drug, nutrient or vitamin into the bloodstream. There is no waiting for them to take effect. In pill form the body will only process a small fraction of the pill, perhaps as low as 10%. The digestive tract will reduce as much as 90% of the pills effectiveness before it is finally absorbed into the bloodstream. Using intra-oral sprays the nutrients are delivered into the bloodstream very rapidly. In certain embodiments, the disclosed compositions may be delivered to a subject intra-orally using delivery by a spray bottle.

Flavoring

One problem with using an intra-oral spray may be the taste of the composition. In one embodiment, peppermint may be used in sufficient amount to mask the flavor of other components of the composition. In other embodiments, other flavor additives for example fruit flavorings or other mint flavorings may be used. In another embodiment, the flavor of a composition may be one palatable to a mammal other than a human such as a dog or cat. These embodiments by no means limit the flavor options of any of the compositions. In other embodiments, the flavor component may be eliminated if the composition is intended for topical application.

Other than human subjects, other mammals may benefit from the effects of an orally delivered insect inhibiting composition. For example, diseases carried by mosquitoes may also affect dogs, cats, horses or birds etc. In one embodiment, a composition may be applied to a household pet prior to exposure to insects. In another embodiment, a composition may be applied to a dog prior to exposure to a species of flea, tick and/or flying insect (e.g. mosquitoes). In yet another embodiment, a composition may be applied to the oral cavity of a dog, cat, horse or bird. In still another embodiment, a composition may be applied orally and/or externally to a horse for inhibiting mosquitoes or flies (e.g. bottle or deer flies).

A composition comprising one or more of the herbs and vitamins disclosed herein may take many forms. These forms include, a portion, including the entire portion of the amounts recommended for inhibiting biting insects. Suitable forms include but are not limited to liquids and lotions. In addition, the composition may take the form of a portion of a predetermined amount such a quarter or a fifth. For example, a liquid formula may require 4 squirts of the liquid of a quarter strength formula for one individual or five squirts for another individual depending on the age and size of the individual. Alternatively, the composition may be in the form of powder-like consistency that can be hydrated and then used as an insect inhibitor. It is to be appreciated that in these other forms (e.g., paste, time-release formula, tablet etc.), the composition may constitute the entire portion of a predetermined amount of the components or a smaller portion of such predetermined amount.

EXAMPLES

The following are exemplary compositions and/or methods for inhibiting a biting insect. For example, one formula (composition) was tested by several subjects for its ability to inhibit insects (e.g. mosquitoes). In addition, one formula was tested for its ability to relieve inflammation of an insect bite area. These formulas may be used to inhibit a variety of biting insects.

Example 1

Insect Inhibitor Composition and Method

In one exemplary embodiment the following amounts of an insect inhibitor composition were administered in the form of a water-based oral spray, using five squirts from a spray bottle. The indicated amounts are the adult dosage.
Choline (Bitartrate) 150 mg
Inositol 150 mg
B-1 Thiamin (Thiamin Mononitrate) 150 mg
B-2 Riboflavin 150 mg
B-3 Niacin (as Niacinamide) 150 mg
B-5 Panothenic Acid (d-calcium pantothenate) 150 mg
B-6 Pyridoxine (pyridoxine HCL) 150 mg
B-9 Folic Acid 400 mcg
B-12 (as cyanocobalamin) 400 mcg
Biotin (d-biotin) 150 mcg
PABA (Para-Aminobenozoic Acid) 1150 mcg
Barley Grass (*Hordeum vulgare*) 500 mg
Lobelia (stem, leaf, flower) 425 mg
*Chlorella* 1000 mg
Base mixture: 50 mg
Base:
Watercress 340 mg
Alfalfa (*medicago sativa*) 450 mg
Parsley (leaf) 450 mg
Lecithin 455 mg
Rice Bran 320 mg In several examples using the above exemplary formula the following doses were applied to prevent insect attack.
Average sized adult: 5 sprays orally
Teen to petite adult: 3 to 4 sprays orally
Child: 2 to 3 sprays orally Infant:—use externally on exposed skin. Avoid spraying in eyes. If eyes are exposed to the spray, wash with cool, clean water.

In preferred embodiments, the composition is administered daily throughout mosquito season. For maximum protection, it may be administered again 1 to 2 hours before being exposed to mosquitoes.

Example 2

Method of Preparation of One Exemplary Composition

Manufacturing Procedure: For 1,000 fluid finished ounces, 12 gallons of Ionized water were put in a sterile 15 gallon doubled walled, stainless steel kettle. A steam generator was used to generate steam inside the double-walled kettle. The water was steam heated to 180 degrees Fahrenheit.

Using a Ohaus electronic weight scale, the following powdered herbs were weighed and mixed into the heated water:
1 kilogram Peppermint
2 kilograms Barley grass
2 kilograms *Lobelia*
4 kilogram *Chorella*
0.2 kilograms Watercress
0.2 kilograms Alfalfa
0.2 kilograms Parsley
0.2 kilograms Rice bran The mix was allowed to set at 180 degrees Fahrenheit for 15 minutes. Turning the valve for cold water to flow inside the double-wall, the mixture was cooled to 120 degrees Fahrenheit and stirred with a Helix Double Rotary Mixer every 3 hours for 12 hours.

Turning the valve for cold water to flow inside the double-wall, the mixture was cooled to 80 degrees Fahrenheit. It was then strained three separate times, using stainless steel filters:
1st—a medium filter,
2nd—a fine filter, and
3rd—an extra fine filter.

Preservative: At 80 degrees Fahrenheit, 0.02% in weight (567 mg) Potassium sorbate was added to retard bacterial growth.

Settling: The mixture was allowed to settle to room temperature in a sterile, polyurethane transfer tank for 72 hours. Next, the liquid was siphoned off from the top with a sterile polyurethane hose to a second sterile, polyurethane tank. It was mixed with a blender and the following vitamins were added:
Choline 1 Kilogram
Inositol 1 Kilogram
B-1 Thiamin Mononitrate 1 Kilogram
B-2 Riboflavin 1 Kilogram
B-3 Niacin 1 Kilogram
B-5 Panothenic Acid 1 Kilogram
B-6 Pyridoxine HCL 1 Kilogram
B-9 Folic Acid 12 grams
B-12 Cyanocobalamin 12 grams
d-biotin 5 grams
Para-Aminobenozoic Acid 30 grams
Lecithin 30 grams The mixture was then mixed with the blender for 5 minutes to produce the final exemplary composition. In one example using a pressurized filling system pump, the liquid of the finished product was bottled. The bottle lids were a mist sprayer with a clear plastic top. Bottles were then labeled and sealed.

Example 3

Administration to Test Subjects

The composition disclosed in Example 2 above was administered as a mosquito inhibitor. Twenty Caucasian adults, 8 males and 12 females, tested the formula over a 2 week period. All reported not being bitten by mosquitoes when they followed directions. When they didn't use the formula and got several bites the subjects administered the formula to the bites prior to going to bed. This topical administration caused the bites to disappear the following day. One subject tested, a Caucasian male of 50, said he did not like the taste and sprayed it on his legs. He said the mosquitoes quit biting him as soon as it was sprayed. Geographic locations of test sites included Texas, Rhode Island, Oregon, Alaska, North Carolina, Florida and Virginia Example 4

Location: Richmond, R.I. Test area: backyard after a barbeque

Two subjects sprayed the formula in their mouths before they left for the barbeque. As the sun went down the neighbors and fellow guests commented on the number of bites they were receiving. The subjects reported that they hadn't noticed the mosquitoes were particularly bad. Once they got home they checked themselves. Neither subject had been bitten.

Example 5

Location:
Emerald Isle, N.C. (Outer Banks)
Test Area: Home on bog surrounded by marsh areas and brackish waters.

The two subjects ate outdoors in the late evening, just prior to sunset. Upon completing dinner, they each had mosquitoes on their legs. They got several bites. Neither of them had used the composition up to that point in time.

Both subjects sprayed the formula into their mouths and returned outdoors a few minutes later, but received some bites so went back indoors. One subject got 8 to 9 bites that evening—however by the next morning they were all gone. This was not typical for the subject, who reported that without the composition mosquito bites usually lingered for up to a week, with itching and scratching.

After administering the composition again on the next day, the subjects allowed sufficient time for the composition to enter their systems. They reported dramatically improved results for mosquito bites.

Example 6

A subject had been taking daily doses (4 sprays) every morning for about a week. On the night of exposure to insects she added a dose of 4 sprays approximately 2 hours prior to venturing outside. Another subject administered a 7 spray dose approximately 2 hours prior and then a 3 spray dose about 1 hour prior to exposure.

The subjects walked outside and down the stairs of a 75-foot embankment. They could feel mosquitoes and other insects flying around and near their bodies. They had a flashlight. The mosquitoes were drawn to the light.

They continued to walk 100 yards along the walkway over the marsh areas that led to the pier, stopping periodically to notice if they were being bitten. No bites, but they could feel flying insects around.

They continued at the walkway junction out over the marshes to the end of the pier for another 100 yards or so. They stayed at the end of the pier for about 7 minutes. During that time they held the flashlight out and saw swarms of mosquitoes in the air. Shining the light on their legs and arms they could see mosquitoes land but they did not bite. At least 4–6 mosquitoes landed on each subject.

They retraced their path back to the house. They were exposed for approximately 25 minutes. The second subject did not have any bites at all on his body. The first subject had one mosquito bite on her left foot and a bite behind her left knee that may or may not have been a mosquito. The second subject stayed outdoors for another 20 to 25 minutes; on the front porch, front yard and back porch, still without receiving any bites.

Example 7

Location: Rhode Island, annual block party on a cul-de-sac surrounded by forest and some wetlands, with substantial mosquito exposure.

The two subjects took a five spray dose every three hours. The subjects did not sustain any bites all evening. It was the first time they did not have to bathe in another externally applied offensive insect spray to remain outside and enjoy the party. Other party guests inquired about the product with interest.

Example 8

In one exemplary embodiment the amounts of a recommended dose of an insect inhibitor formula may be in the following range:
- about 100 to 425 mg of peppermint;
- about 200 to 850 mg of barley grass;
- about 200 to 850 mg of *lobelia;*
- about 500 to 2000 mg of *chlorella;*
- about 20 to 85 mg of watercress;
- about 20 to 85 mg of alfalfa;
- about 20 to 85 mg of parsley;
- about 20 to 85 mg of rice bran;
- about 75 to 300 mg of thiamin (B-1);
- about 75 to 300 mg of riboflavin (B-2);
- about 75 to 300 mg of niacin (B-3);
- about 75 to 300 mg of panothenic acid (B-5);
- about 75 to 300 mg of pyridoxine (B-6);
- about 200 to 800 µg of folic acid (B-9);
- about 200 to 800 µg of cyanocobalamin (B-12);
- about 75 to 300 mg of choline;
- about 75 to 300 mg of inositol;
- about 75 to 300 µg of d-biotin;
- about 575 to 2300 µg of para-aminobenzoic acid; and
- about 575 to 2300 µg of lecithin.

The composition may be used in a variety of applications, such as an oral or topical administration of use to inhibit insects. In another embodiment, one range of the components of the above formula may be used to inhibit mosquitoes. In another embodiment, one range of the components of the above formula may be used as an orally administered insect inhibitor to inhibit mosquitoes and other insects from biting subjects.

Example 9

Two adult subjects, one male and one female, went on a camping trip to Grand Teton National Park in Wyoming. The subjects did not use any topical mosquito repellant. On the first day, subjects each took an oral dose of 5 sprays of the composition disclosed in Example 8, about 30 minutes before walking in a mosquito-infested area of the Park. Subjects suffered a number of mosquito bites, about 20 bites each. Subjects continued to take oral doses of 5 sprays each per day. The subjects noticed that on the second day, they only suffered a few bites each. By the third day, they only suffered one bite each and on the fourth and fifth days of use of the composition they did not notice any mosquito bites, despite returning to the same area where they had received multiple bites the first day. Subjects concluded that the efficacy of the insect inhibitor composition was increased with usage on consecutive days.

Subjects further noticed that on the second day of the camping trip, after having been bitten about 20 times the previous day, they had no symptoms of swelling, redness or itching in the bitten areas. Subjects were very surprised by this, as they expected to have numerous welts and severe itching following that number of mosquito bites. The female subject commented that she always had a severe reaction to mosquito bites, with intense itching, redness and swelling. The female subject was highly allergic to insect toxins and had previously experienced symptoms of incipient anaphylactic shock upon exposure to bee or wasp stings. On subsequent days, subjects noticed that even when they were bitten by mosquitoes, they experienced relatively little itching and no swelling and the insect bites showed no signs of redness, itching or swelling by the day following the bite.

What is claimed is:

1. A composition comprising:
   peppermint;
   barley grass;
   *lobelia;*
   *chlorella;*
   watercress;
   alfalfa;
   parsley;
   rice bran;
   thiamin (B-1);
   riboflavin (B-2);
   niacin (B-3);
   pantothenic acid (B-5);
   pyridoxine (B-6);
   folic acid (B-9);
   cyanocobalamin (B-12);
   choline;
   inositol;
   d-biotin;
   para-aminobenzoic acid; and
   lecithin
wherein said composition inhibits insects from biting a subject after oral administration of the composition to the subject.

2. The composition of claim 1, wherein said insects are mosquitoes.

3. The composition of claim 1, wherein said composition inhibits insects from biting when administered as a spray to the oral cavity.

4. The composition of claim 1, wherein the peppermint, barley grass, *lobelia, chlorella*, watercress, alfalfa, parsley and rice bran are in the form of an extract, concentrate, decoction, infusion, homogenate, essence or distillate.

5. The composition of claim 1, wherein the composition reduces swelling, inflammation and/or itching of the localized area around an insect bite.

6. The composition of claim 5, wherein the composition eliminates swelling, inflammation and/or itching of the localized area around an insect bite within a one day period following the bite.

7. The composition of claim 1, wherein the subject is a human, a dog, a cat or a horse.

8. The composition of claim 1, comprising:
   about 100 to 425 mg of peppermint;
   about 200 to 850 mg of barley grass;
   about 200 to 850 mg of *lobelia*;
   about 500 to 2000 mg of *chlorella*;
   about 20 to 85 mg of watercress;
   about 20 to 85 mg of alfalfa;
   about 20 to 85 mg of parsley;
   about 20 to 85 mg of rice bran;
   about 75 to 300 mg of thiamin (B-1);
   about 75 to 300 mg of riboflavin (B-2);
   about 75 to 300 mg of niacin (B-3);
   about 75 to 300 mg of panothenic acid (B-5);
   about 75 to 300 mg of pyridoxine (B-6);
   about 200 to 800 µg of folic acid (B-9);
   about 200 to 800 µg of cyanocobalamin (B-12);
   about 75 to 300 mg of choline;
   about 75 to 300 mg of inositol;
   about 75 to 300 µg of d-biotin;
   about 575 to 2300 µg of para-aminobenzoic acid; and
   about 575 to 2300 µg of lecithin.

9. An insect inhibitor kit comprising:
   a) a container capable of administering a liquid as a spray; and
   b) a liquid form of the composition of claim 1.

* * * * *